(12) United States Patent
Willey et al.

(10) Patent No.: US 6,352,562 B1
(45) Date of Patent: Mar. 5, 2002

(54) METHOD OF CLEANING FABRICS USING BLEACHING COMPOUNDS COMPRISING SUBSTITUTED BENZOYL CAPROLACTAM BLEACH ACTIVATORS

(75) Inventors: Alan David Willey, Cincinnati; Michael Eugene Burns, West Chester, both of OH (US)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 09/712,744

(22) Filed: Nov. 14, 2000

Related U.S. Application Data

(62) Division of application No. 08/469,741, filed on Jun. 6, 1995, now Pat. No. 6,197,737, which is a continuation of application No. 08/064,562, filed on May 20, 1993, now abandoned.

(51) Int. Cl.[7] ............................... D06L 3/04; C11D 3/00
(52) U.S. Cl. ................. 8/111; 8/101; 8/107; 252/186.1; 252/186.39; 510/302; 510/376
(58) Field of Search ............................. 8/101, 107, 111; 510/302, 376; 252/186.1, 186.38, 186.39

(56) References Cited

U.S. PATENT DOCUMENTS

| | | | |
|---|---|---|---|
| 3,042,621 A | 7/1962 | Kirschenbauer | 252/99 |
| 3,075,921 A | 1/1963 | Brocklehurst | 252/99 |
| 3,177,148 A | 4/1965 | Bright et al. | 252/99 |
| 3,637,339 A | 1/1972 | Gray | 8/111 |
| 4,013,575 A | 3/1977 | Catrantas et al. | 252/104 |
| 4,299,716 A | 11/1981 | Cottrell et al. | 252/99 |
| 4,545,784 A | 10/1985 | Sanderson | 8/107 |
| 4,606,838 A | 8/1986 | Burns | 252/94 |
| 4,852,898 A | 8/1989 | Burns | 252/102 |
| 5,755,992 A * | 5/1998 | Jeffrey et al. | 252/186.38 |
| 5,932,532 A * | 8/1999 | Willey et al. | 510/302 |

FOREIGN PATENT DOCUMENTS

| | | | |
|---|---|---|---|
| EP | 257700 | 3/1988 | 252/99 |
| GB | 1596313 | 8/1981 | D06F/39/02 |
| GB | 2189520 | 10/1987 | |

OTHER PUBLICATIONS

Aikawa, T. et al. "Herbicidal activity of caprolactam derivatives" *J. Fac. Agric*, 1976 (20(2) 75–78. Chem Abstract vol 85, No. 1, 1086z, Jul. 1976.

* cited by examiner

*Primary Examiner*—Yogendra N. Gupta
*Assistant Examiner*—Derrick G Hamlin
(74) *Attorney, Agent, or Firm*—C. Brant Cook; Kim W. Zerby; Steven W. Miller

(57) ABSTRACT

Method for cleaning fabrics using laundry detergents and bleaching systems which comprise substituted benzoyl caprolactam bleach activators are presented. The bleach activators are effective under mixed soil conditions, especially mixtures of hydrophobic and hydrophilic soils and stains.

9 Claims, No Drawings

METHOD OF CLEANING FABRICS USING BLEACHING COMPOUNDS COMPRISING SUBSTITUTED BENZOYL CAPROLACTAM BLEACH ACTIVATORS

CROSS REFERENCE

This application is a Divisional of pending Application Ser. No. 08/469,741, filed Jun. 6, 1995 U.S. Pat. No. 6,197,737, which is a Continuation of Application Ser. No. 08/064562, filed May 20, 1993, now abandoned.

FIELD OF THE INVENTION

The present invention relates to a method of cleaning fabrics using laundry detergents and bleaching systems which comprise novel substituted benzoyl caprolactam bleach activators.

BACKGROUND OF THE INVENTION

It has long been known that peroxygen bleaches are effective for stain and/or soil removal from fabrics, but that such bleaches are temperature dependent. At a laundry liquor temperature of 60° C., peroxygen bleaches are only partially effective. As the laundry liquor temperature is lowered below 60° C., peroxygen bleaches become relatively ineffective. As a consequence, there has been a substantial amount of industrial research to develop bleaching systems which contain an activator that renders peroxygen bleaches effective at laundry liquor temperatures below 60° C.

Numerous substances have been disclosed in the art as effective bleach activators. One widely-used bleach activator is tetraacetyl ethylene diamine (TAED). TAED provides effective hydrophilic cleaning especially on beverage stains, but has limited performance on dingy stains and body soils. Another type of activator, such as nonanoyloxybenzenesulfonate (NOBS) and other activators which generally comprise long chain alkyl moieties, is hydrophobic in nature and provides excellent performance on dingy stains. However, many of the hydrophobic activators developed thus far can promote damage to natural rubber parts used in certain washing machines and to natural rubber articles exposed to the activators. Because of these negative effects on natural rubber machine parts and articles, the selection of such detergent-added bleaching systems has been limited.

It has now been determined that in conventional bleaching systems, particularly those comprising a hydrophobic bleach activator and a source of hydrogen peroxide, the bleach activator undergoes perhydrolysis to form a peroxyacid bleaching agent. A by-product of the perhydrolysis reaction between such bleach activators and hydrogen peroxide is a diacylperoxide (DAP) species. It has now further been discovered that the DAP's derived from hydrophobic activators tend to be insoluble, poorly dispersible, oily materials which form a residue which can deposit on the natural rubber machine parts that are exposed to the laundry liquor. The oily DAP residue can form a film on the natural rubber parts and promote free radical and peroxide damage to the rubber, which eventually leads to failure of the part. This is particularly true of rubber parts which have prolonged exposure to the laundry liquor, such as sump hoses.

By the present invention, is has now been discovered that the class of bleach activators derived from substituted benzoyl caprolactams forms peroxyacids upon perhydrolysis without the production of oily, harmful DAP's. Without intending to be limited by theory, it is believed that the bleach activators employed herein provide good cleaning performance with safety to natural rubber, since they do not expose the natural rubber machine parts or articles to DAP oxidation. Whatever the reason, natural rubber parts and articles remain substantially undamaged by the bleaching systems of the present invention.

By the present invention, it has also now been discovered that the substituted benzoyl caprolactam bleach activators of this invention provide both hydrophilic and hydrophobic cleaning, including dingy soil clean-up and enhanced nucleophilic and body soil removal. Furthermore, the bleaching systems and activators herein are effective at low concentration levels and at temperatures below 60° C. which affords less color damage to fabrics than other activators when used in the manner provided by this invention.

Accordingly, the present invention solves the long-standing need for an effective, color-safe, hydrophobic and hydrophilic bleaching system which does not promote damage to natural rubber parts in washing machines or damage to natural rubber articles.

BACKGROUND ART

U.S. Pat. No. 4,545,784, Sanderson, issued Oct. 8, 1985, discloses the adsorption of activators onto sodium perborate monohydrate.

SUMMARY OF THE INVENTION

The present invention relates to a method of cleaning fabrics using substituted benzoyl caprolactam bleach activators in bleaching systems and laundry detergents. The substituted benzoyl caprolactams have the formula:

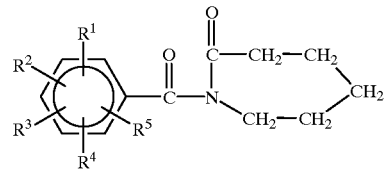

wherein $R^1$, $R^2$, $R^3$, $R^4$, and $R^5$ contain from 1 to 12 carbon atoms, preferably from 1 to 6 carbon atoms and are members selected from the group consisting of H, halogen, alkyl, alkoxy, alkoxyaryl, alkaryl, alkaryloxy, and members having the structure:

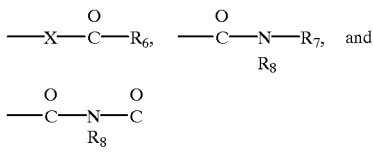

wherein $R_6$ is selected from the group consisting of H, alkyl, alkaryl, alkoxy, alkoxyaryl, alkaryloxy, and aminoalkyl; X is O, NH, or $NR_7$, wherein $R_7$ is H or a $C_1$–$C_4$ alkyl group; and $R_8$ is an alkyl, cycloalkyl, or aryl group containing from 3 to 11 carbon atoms; provided that at least one R substituent is not H.

In a preferred embodiment, $R^1$, $R^2$, $R^3$, and $R^4$ are H and $R^5$ is selected from the group consisting of methyl, methoxy, ethyl, ethoxy, propyl, propoxy, isopropyl, isopropoxy, butyl, tert-butyl, butoxy, tert-butoxy, pentyl, pentoxy, hexyl, hexoxy, Cl, and $NO_3$. In another preferred embodiment, $R^1$, $R^2$, $R^3$ are H, and $R^4$ and $R^5$ are members selected from the group consisting of methyl, methoxy, and Cl.

The invention also relates to bleaching systems and laundry detergents comprising the bleach activators. Said bleaching system comprises:
 a) at least about 0.1%, preferably from about 1% to about 75%, by weight, of a peroxygen bleaching compound capable of yielding hydrogen peroxide in an aqueous solution;
 b) at least about 0.1%, preferably from about 0.1% to about 50%, by weight, of one or more substituted benzoyl caprolactam bleach activators having the formula:

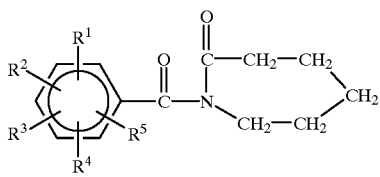

wherein $R^1$, $R^2$, $R^3$, $R^4$, and $R^5$ are as defined above.

The peroxygen bleaching compound can be any peroxide source, and is preferably a member selected from the group consisting of sodium perborate monohydrate, sodium perborate tetrahydrate, sodium pyrophosphate peroxyhydrate, urea peroxyhydrate, sodium percarbo- nate, sodium peroxide and mixtures thereof. Highly preferred peroxygen bleaching compounds are selected from the group consisting of sodium perborate monohydrate, sodium perborate tetrahydrate, sodium percarbonate and mixtures thereof. The most highly preferred peroxygen bleaching compound is sodium percarbonate.

The invention also encompasses laundry compositions in granular, paste, liquid, or bar form which comprise the aforesaid bleaching system together with detergent ingredients which are present in the composition at the levels indicated hereinafter.

The substituted benzoyl caprolactam herein can also be used in combination with other bleach activators, such as N-alkyl capro- lactam, unsubstituted benzoyl caprolactam, tetraacetyl ethylene diamine, alkanoxybenzenesulfonate, including nonanoyloxybenzene- sulfonate, benzoxazin-type bleach activators, and peroxyacid agents and activators having amide moieties.

The bleaching method herein is preferably conducted with agitation of the fabrics with an aqueous liquor containing the aforesaid bleaching system at levels from about 50 ppm to about 27,500 ppm. The method can be carried out at any desired washing temperature, even at temperatures below about 60° C., and is readily conducted at temperatures in the range of from about 5° C. to about 45° C. The method can be conducted conveniently using a composition which is in bar form, but can also be conducted using granules, flakes, powders, pastes, and the like.

The aqueous laundry liquor typically comprises at least about 300 ppm of conventional detergent ingredients, as well as at least about 25 ppm of the bleaching compound and at least about 25 ppm of a bleach activator. Preferably, the liquor comprises from about 900 ppm to about 20,000 ppm of conventional detergent ingredients, from about 100 ppm to about 25,000 ppm of the bleaching compound and from about 100 ppm to about 2,500 ppm of the bleach activator. The conventional detergent ingredients and bleaching system will typically be combined into a detergent composition such as a granular laundry detergent or laundry detergent bar.

The conventional detergent ingredients employed in said method and in the compositions herein comprise from about 1% to about 99.8%, preferably from about 5% to about 80%, of a detersive surfactant. Optionally, the detergent ingredients comprise from about 5% to about 80% of a detergent builder. Other optional detersive adjuncts can also be included in such compositions at conventional usage levels.

All percentages, ratios, and proportions herein are by weight, unless otherwise specified. All documents cited are incorporated herein by reference.

DETAILED DESCRIPTION OF THE INVENTION

The bleaching system employed in the present invention provides effective and efficient surface bleaching of fabrics which thereby removes stains and/or soils from the fabrics. The bleaching system is particularly efficient at cleaning a mixture of soil loads, especially mixtures of hydrophobic and hydrophilic soils. Hydrophobic soils are generally associated with nucleophilic, lipid and protein-based soils and stains, such as body soils, blood, etc., but are also effective on so-called "dingy soils". Dingy soils are those that build up on textiles after numerous cycles of usage and washing, and result in a gray or yellow tint on white fabrics. Hydrophilic soils include food and beverage stains. Further, the bleaching system is safe to natural rubber machine parts and articles.

Substituted benzoyl caprolactams have been found to be unique among the bleach activator compounds, inasmuch as they appear to exhibit both hydrophobic and hydrophilic bleaching activity. This hydrophobic/hydrophilic bleaching capability makes substituted benzoyl caprolactams the activators of choice for the formulator who is seeking broad spectrum bleaching activity, and wishes to use a single caprolactam activator in the bleaching system.

The bleaching mechanism and, in particular, the surface bleaching mechanism are not completely understood. However, it is generally believed that the bleach activator undergoes nucleophilic attack by a perhydroxide anion, which is generated from the hydrogen peroxide evolved by the peroxygen bleaching compound, to form a peroxycarboxylic acid. This reaction is commonly referred to as perhydrolysis. It is also believed, that the bleach activators within this invention can render peroxygen bleaches more efficient even at laundry liquor temperatures wherein bleach activators are not necessary to activate the bleach, i.e., above about 60° C. Therefore, with bleach systems of the invention, less peroxygen bleach is required to achieve the same level of surface bleaching performance as is obtained with the peroxygen bleach alone.

The components of the bleaching system herein comprise the bleach activator and the peroxide source, as described hereinafter.

Bleach Activators

Methods of making substituted benzoyl caprolactams are illustrated by the laboratory syntheses presented in Examples I and II.

Examples of preferred substitiuted benzyol caprolactams include methylbenzoyl caprolactam, ethylbenzoyl caprolactam, ethoxybenzoyl caprolactam, propylbenzoyl caprolactam, propoxy- benzoyl caprolactam, isopropylbenzoyl caprolactam, isoprop- oxybenzoyl caprolactam, butylbenzoyl caprolactam, butoxybenzoyl caprolactam, tert-butylbenzoyl caprolactam, tert-butoxybenzoyl caprolactam, pentylbenzoyl caprolactam, pentoxybenzoyl caprolactam, hexylbenzoyl caprolactam, hexoxybenzoyl caprolactam, 2,4,6-tri- chlorobenzoyl caprolactam, pentafluorobenzoyl caprolactam, dichlo- robenzoyl caprolactam, dimethoxybenzoyl caprolactam, 4-nitrobenzoyl caprolactam, 3-chlorobenzoyl caprolactam, 4-chlorobenzoyl caprolactam, 2,4-dichlorobenzoyl caprolactam, terephthaloyl dicapro- lactam, and mixtures thereof.

The bleaching system comprises at least about 0.1%, preferably from about 0.1% to about 50%, more preferably from about 1% to about 30%, most preferably from about 3% to about 25%, by weight, of one or more substitued benzoyl caprolactam bleach activator.

When the activators are used, optimum surface bleaching performance is obtained when the pH of the aqueous wash liquor is between about 7.0 and about 10.5, preferably from about 7.0 to about 9.5, most preferably from about 7.5 to about 8.5 in order to facilitate the perhydrolysis reaction. Such pH can be obtained with substances commonly known as buffering agents, which are optional components of the bleaching systems herein.

The bleaching and stain removal performance of the organic peroxyacids, obtained from the bleach activators by the perhydroly- sis reaction, is typically optimal at the pKa of the peroxyacid. The pKa is defined as the pH at which the concentration of the peroxyacid and the peroxyacid anion are equal. The organic peroxyacids are weaker acids than the corresponding peroxyacids, and typically exhibit pKa's in the range of about 7 to about 8.5. Examples of organic peroxyacids derived from this invention and their pKa's are 4-methoxyperoxybenzoic acid (pKa=8.1), 4-methylperoxybenzoic acid (pKa=8.0), 4-chloroperoxybenzoic acid (pKa=7.7), 3-chloroperoxybenzoic acid (pKa=7.6), and 4-nitroperoxybenzoic acid (pKa=7.3). (see *Organic Peroxides*, Volume I, D. Swern, Editor, Wiley-Interscience, 1970.)

Since the pKa's of the peroxyacids are approximately neutral and the perhydrolysis reaction is fastest at alkaline pH's, it is often desirable to employ, as a portion of the bleaching system formulation, a pH reduction system. A pH reduction system is one that can release acid to the wash, resulting in a decreasing pH over time. The pH reduction system can release acid by either a chemical reaction in situ or by controlled release of acidic components that are physically entrained, for example, by encapsulation or by coating with water soluble materials. When the wash pH is reduced at a controlled rate by incorporation of a pH reduction system, the bleach activator is first allowed to undergo perhydrolysis at an alkaline pH so as to form the organic peroxyacid. Then, as the pH of the wash is decreased by the pH reduction system, the wash environment approaches a pH in which the bleaching performance of the organic peroxyacid is maximized.

The Peroxygen Bleaching Compound

The peroxygen bleaching compounds useful herein are those capable of yielding hydrogen peroxide in an aqueous liquor. These compounds are well known in the art and include hydrogen peroxide and the alkali metal peroxides, organic peroxide bleaching compounds such as urea peroxide, and inorganic persalt bleaching compounds, such as the alkali metal perborates, percarbonates, perphosphates, and the like. Mixtures of two or more such bleaching compounds can also be used, if desired.

Preferred peroxygen bleaching compounds include sodium perborate, commercially available in the form of mono-, tri-, and tetra-hydrate, sodium pyrophosphate peroxyhydrate, urea peroxy-hydrate, sodium peroxide, and sodium percarbonate. Particularly preferred are sodium perborate tetrahydrate, sodium perborate monohydrate and sodium percarbonate. Sodium percarbonate is especially preferred because it is very stable during storage and yet still dissolves very quickly in the bleaching liquor. It is believed that such rapid dissolution results in the formation of higher levels of percarboxylic acid and, thus, enhanced surface bleaching performance.

Highly preferred percarbonate can be in uncoated or coated form. The average particle size of uncoated percarbonate ranges from about 400 to about 1200 microns, most preferably from about 400 to about 600 microns. If coated percarbonate is used, the preferred coating materials include mixtures of carbonate and sulphate, silicate, borosilicate, or fatty carboxylic acids.

The bleaching system comprises at least about 0.1%, preferably from about 1% to about 75%, more preferably from about 3% to about 40%, most preferably from about 3% to about 25%, by weight, of a peroxygen bleaching compound capable of yielding hydrogen peroxide in an aqueous solution.

The weight ratio of bleach activator to peroxygen bleaching compound in the bleaching system typically ranges from about 2:1 to 1:5. In preferred embodiments, the ratio ranges from about 1:1 to about 1:3.

The bleach activator/bleaching compound systems herein are useful per se as bleaches. However, such bleaching systems are especially useful in compositions which can comprise various detersive adjuncts such as surfactants, builders, enzymes, and the like as disclosed hereinafter.

Detersive Surfactant

The amount of detersive surfactant included in the fully-formulated detergent compositions afforded by the present invention can vary from about 1% to about 99.8%, by weight of the detergent ingredients, depending upon the particular surfactants used and the effects desired. Preferably, the detersive surfactants comprise from about 5% to about 80%, by weight of the detergent ingredients.

The detersive surfactant can be nonionic, anionic, ampholytic, zwitterionic, or cationic. Mixtures of these surfactants can also be used. Preferred detergent compositions comprise anionic detersive surfactants or mixtures of anionic surfactants with other surfactants, especially nonionic surfactants.

Nonlimiting examples of surfactants useful herein include the conventional $C_{11}$–$C_{18}$ alkyl benzene sulfonates and primary, secondary, and random alkyl sulfates, the $C_{10}$–$C_{18}$ alkyl alkoxy sulfates, the $C_{10}$–$C_{18}$ alkyl polyglycosides and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. Other conventional useful surfactants are listed in standard texts.

One particular class of adjunct nonionic surfactants especially useful herein comprises the polyhydroxy fatty acid amides of the formula:

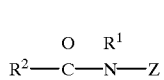

(I)

wherein: $R^1$ is H, $C_1$–$C_8$ hydrocarbyl, 2-hydroxyethyl, 2-hydroxypropyl, or a mixture thereof, preferably $C_1$–$C_4$ alkyl, more preferably $C_1$ or $C_2$ alkyl, most preferably $C_1$ alkyl (i.e., methyl); and $R^2$ is a $C_5$–$C_{32}$ hydrocarbyl moiety, preferably straight chain $C_7$–$C_{19}$alkyl or alkenyl, more preferably straight chain $C_9$–$C_{17}$ alkyl or alkenyl, most preferably straight chain $C_{11}$–$C_{19}$ alkyl or alkenyl, or mixture thereof; and Z is a polyhydroxyhydrocarbyl moiety having a linear hydrocarbyl chain with at least 2 (in the case of glyceraldehyde) or at least 3 hydroxyls (in the case of other reducing sugars) directly connected to the chain, or an alkoxylated derivative (preferably ethoxylated or propoxylated) thereof. Z preferably will be derived from a reducing sugar in a reductive amination reaction; more preferably Z is a glycityl moiety. Suitable reducing sugars include glucose, fructose, maltose, lactose, galactose, mannose, and xylose, as well as glyceraldehyde. As raw materials, high dextrose corn syrup, high fructose corn syrup, and high maltose corn syrup can be utilized as well as the individual sugars listed above. These corn syrups may yield a mix of sugar components for Z. It should be understood that it is by no means intended to exclude other suitable raw materials. Z preferably will be selected from the group consisting of —$CH_2$—$(CHOH)_n$—$CH_2OH$, —CH($CH_2OH$)—$(CHOH)_{n-1}$—$CH_2OH$, —$CH_2$—$(CHOH)_2$(CHOR')—(CHOH)—$CH_2OH$, where n is an integer from 1 to 5, inclusive, and R' is H or a cyclic mono- or polysaccharide, and alkoxylated derivatives thereof. Most preferred are glycityls wherein n is 4, particularly —$CH_2$—$(CHOH)_4$—$CH_2OH$.

In Formula (I), $R^1$ can be, for example, N-methyl, N-ethyl, N-propyl, N-isopropyl, N-butyl, N-isobutyl, N-2-hydroxy ethyl, or N-2-hydroxy propyl. For highest sudsing, $R^1$ is preferably methyl or hydroxyalkyl. If lower sudsing is desired, $R^1$ is preferably $C_2$–$C_8$ alkyl, especially n-propyl, iso-propyl, n-butyl, iso-butyl, pentyl, hexyl and 2-ethyl hexyl.

$R_2$—CO—N< can be, for example, cocamide, stearamide, oleamide, lauramide, myristamide, capricamide, palmitamide, tallowamide, etc.

Detergent Builders

Optional detergent ingredients employed in the present invention contain inorganic and/or organic detergent builders to assist in mineral hardness control. If used, these builders comprise from about 5% to about 80% by weight of the detergent compositions.

Inorganic detergent builders include, but are not limited to, the alkali metal, ammonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. However, non-phosphate builders are required in some locales.

Examples of silicate builders are the alkali metal silicates, particularly those having a $SiO_2$:$Na_2O$ ratio in the range 1.6:1 to 3.2:1 and layered silicates, such as the layered sodium silicates described in U.S. Pat. No. 4,664,839, issued May 12, 1987 to H. P. Rieck, available from Hoechst under the trademark "SKS"; SKS-6 is an especially preferred layered silicate builder.

Carbonate builders, especially a finely ground calcium carbonate with surface area greater than 10 $m^2/g$, are preferred builders that can be used in granular compositions. The density of such alkali metal carbonate built detergents can be in the range of 450–850 g/l with the moisture content preferably below 4%. Examples of carbonate builders are the alkaline earth and alkali metal carbonates as disclosed in German Patent Application No. 2,321,001 published on Nov. 15, 1973.

Aluminosilicate builders are especially useful in the present invention. Preferred aluminosilicates are zeolite builders which have the formula:

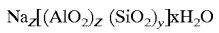

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P (B), and Zeolite X. Preferably, the aluminosilicate has a particle size of about 0.1–10 microns in diameter.

Organic detergent builders suitable for the purposes of the present invention include, but are not restricted to, a wide variety of polycarboxylate compounds, such as ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987.

Other useful detergent builders include the ether hydroxypolycarboxylates, copolymers of maleic anhydride with ethylene or vinyl methyl ether, 1, 3, 5-trihydroxy benzene-2, 4, 6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Citrate builders, e.g., citric acid and soluble salts thereof (particularly sodium salt), are preferred polycarboxylate builders that can also be used in granular compositions, especially in combination with zeolite and/or layered silicate builders.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Optional Detersive Adjuncts

As a preferred embodiment, the conventional detergent ingredients employed herein can be selected from typical detergent composition components such as detersive surfactants and detergent builders. Optionally, the detergent ingredients can include one or more other detersive adjuncts or other materials for assisting or enhancing cleaning performance, treatment of the substrate to be cleaned, or to modify the aesthetics of the detergent composition. Usual detersive adjuncts of detergent compositions include the ingredients set forth in U.S. Pat. No. 3,936,537, Baskerville et al. Adjuncts which can also be included in detergent compositions employed in the present invention, in their conventional art-established levels for use (generally from 0% to about 20% of the detergent ingredients, preferably from about 0.5% to about 10%), include enzymes, especially proteases, lipases and cellulases, color speckles, suds boosters, suds suppressors, antitarnish and/or anticorrosion agents, soil-suspending agents, soil release agents, dyes, fillers, optical brighteners, germicides, alkalinity sources, hydrotropes, antioxidants, enzyme stabilizing agents, perfumes, solvents, solubilizing agents, clay soil removal/anti-redeposition agents, polymeric dispersing agents, processing aids, fabric softening components static control agents, etc.

Bleach systems optionally, but preferably, will also comprise a chelant which not only enhances bleach stability by scavenging heavy metal ions which tend to decompose bleaches, but also assists in the removal of polyphenolic stains such as tea stains, and the like. Various chelants, including the aminophosphonates, available as DEQUEST from Monsanto, the nitrilotriacetates, the hydroxyethyl-ethylenediamine triacetates, and the like, are known for such use. Preferred biodegradable, non-phosphorus chelants include ethylenediamine disuccinate ("EDDS"; see U.S. Pat. No. 4,704,233, Hartman and Perkins), ethylenediamine-N,N'-diglutamate (EDDG) and 2-hydroxypropylenediamine-N,N'-disuccinate (HPDDS) compounds. Such chelants can be used in their alkali or alkaline earth metal salts, typically at levels from about 0.1% to about 10% of the present compositions.

Optionally, the detergent compositions employed herein can comprise, in addition to the bleaching system of the present invention, one or more other conventional bleaching agents, activators, or stabilizers. In general, the formulator will ensure that the bleach compounds used are compatible with the detergent formulation. Conventional tests, such as tests of bleach activity on storage in the presence of the separate or fully-formulated ingredients, can be used for this purpose.

Specific examples of optional bleach activators for incorporation in this invention include tetraacetyl ethylene diamine (TAED), alkanoyloxybenzenesulfonates, including nonanoyloxybenzene- sulfonate and benzoyloxybenzenesulfonate, the benzoxazin-type bleaching activators disclosed in U.S. Pat. No. 4,966,723, Hodge et al, issued Oct. 30, 1990, and the peroxyacid agents and activators having amide moieties disclosed in U.S. Pat. No. 4,634,551, Bums et al, issued Jan. 6, 1987. Such bleaching compounds and agents can be optionally included in detergent compositions in their conventional art-established levels of use, generally from 0% to about 15%, by weight of detergent composition.

Bleaching activators of the invention are especially useful in conventional laundry detergent compositions such as those typically found in granular detergents or laundry bars. U.S. Pat. No. 3,178,370, Okenfuss, issued Apr. 13, 1965, describes laundry detergent bars and processes for making them. Philippine Patent 13,778, Anderson, issued Sept. 23, 1980, describes synthetic detergent laundry bars. Methods for making laundry detergent bars by various extrusion methods are well known in the art.

The following examples are given to further illustrate the present invention, but are not intended to be limiting thereof.

EXAMPLE I

Synthesis of 4-ethoxybenzoyl caprolactam—To a 500 ml flask equipped with a reflux condenser and overhead stirrer is charged 0.18 moles of 4-ethoxybenzoic acid, 200 ml of chloroform, and 0.54 moles of thionyl chloride. The resulting solution is heated to reflux, refluxed with stirring for 3 hrs, and then stirred at room termperature for 18 hrs. The chloroform is removed by rotary evaporation to yield the acid chloride (0.18 moles). A one liter 3-neck flask is fitted with an addition funnel, reflux condenser, and mechanical stirrer. The flask is charged with 0.18 moles of caprolactam, triethyl amine (0.20 moles) and 450 ml of p-dioxane. The acid chloride is added as a solution in 50 ml p-dioxane over a period of 15 min. The resulting mixture is refluxed for 3.5 hrs. After cooling to room temperature, the precipitated solid is filtered and the dioxane removed by rotary evaporation. The residue is recrystallized from chloroform to yield 0.13 moles of 4-ethoxybenzoyl caprolactam, which NMR analysis shows to be 93% pure. The 4-ethoxybenzoyl caprolactam has a melting point of 108–111° C. $^1$H NMR reveals 1.4 ppm (t, 3H); 1.8 ppm (m, 6H); 2.7 ppm (m, 2H); 3.9 ppm (m, 2H); 4 ppm (q, 2H), 6.9 ppm (d, 2H); 7.6 ppm (d, 2H). $^{13}$C NMR provides 15 ppm (s); 24 ppm (s); 29 ppm (d); 39 ppm (s); 46 ppm (s); 64 ppm (s); 114 ppm (s); 128 ppm (s); 131 ppm (s); 162 ppm (s); 174 ppm (s); 178 ppm (s). IR (cm$^{-1}$) at 2930, 1667, 1604, 1254.

EXAMPLE II

Synthesis of 4-nitrobenzoyl caprolactam—To a 1 liter flask equipped with drying tybe, condenser, and overhead stirrer is charged 0.3 moles of 4-nitrobenzoyl chloride, 0.3 moles of caprolactam, 0.33 moles of triethylamine and 300 ml of toluene. The resultant mixture is heated to reflux, refluxed with stirring for 6 hours, cooled and filtered. The filtrate is washed with 3×25 ml of water and dried over anhydrous magnesium sulphate. To the filtrate is added 500 ml of hexane, and after stirring for 20 minutes, the resultant precipitate is collected via vacuum filtration to yield 0.15 moles of 4-nitrobenzoyl caprolactam which NMR analysis shows to be 95% pure. The 4-nitrobenzoyl caprolactam has a melting point of 102° C. $^1$H NMR reveals 1.8 ppm (Broad s, 6H); 2.7 ppm (m, 2H); 4 ppm (m, 2H); 7.6 ppm (d, 2H); 8.2 ppm (d, 2H). $^{13}$C NMR provides 24 ppm (s); 29 ppm (d); 39 ppm (s); 45 ppm (s); 123 ppm (s); 128 ppm (s); 143 ppm (s); 148 ppm (s); 172 ppm (s); 177 ppm (s). IR (cm$^{-1}$) at 2934, 1681, 1602, 1522, 1348.

EXAMPLE III

Synthesis of 3-chlorobenzoyl caprolactam—To a 1 liter flask equipped with argon sweep, condenser and overhead stirrer is charged 0.25 moles of caprolactam, 0.275 moles of triethylamine, and 200 ml of toluene. The resultant mixture is heated to reflux. A solution of 0.25 moles of 3-chlororbenzoyl chloride in 50 ml of toluene is added over 30 minutes, and the mixture refluxed with stirring for 6 hours, cooled and filtered. The filtrate is washed with 3×50 ml of water and dried over anhydrous magnesium sulphate. To the filtrate is added 500 ml of hexane, and the resultant solution placed in a freezer for 6 hours. After which time, the resultant precipitate is collected via vacuum filtration to yield 0.14 moles of 3-chlorobenzoyl caprolactam which NMR analysis shows to be 98% pure. The 3-chlorobenzoyl caprolactam has a melting point of approximately 69–73° C. $^1$H NMR reveals 1.8 ppm (Broad s, 6H); 2.7 ppm (m, 2H); 4 ppm (m, 2H); 7.4 ppm (m, 4H). $^{13}$C NMR provides 24 ppm (s); 29 ppm (d); 39 ppm (s); 45 ppm (s); 126 ppm (s);

128 ppm (s); 129 ppm (s); 131 ppm (s); 134 ppm (s); 138 ppm (s); 173 ppm (s), and 178 ppm (s). IR (cm$^{-1}$) at 2932, 1681, 1262.

EXAMPLE IV

Synthesis of 4-butoxybenzoyl caprolactam—To a 500 ml flask equipped with drying tube, condenser and overhead stirrer is charged 0.13 moles of 4-butoxybenzoic acid, 0.39 moles of thionyl chloride, and 150 ml of diethyl ether. The resultant mixture is heated to reflux, and the mixture is refluxed with stirring for 3 hours and cooled. The diethyl ether and excess thionyl chloride is is removed by rotary evaporation to yield the acid chloride (0.13 moles).

To a 1 liter flask equipped with drying tube, condenser and overhead stirrer is charged 0.13 moles of caprolactam, 0.16 moles of triethylamine and 150 ml of dioxane. The resultant solution is heated to reflux, and a solution of 0.13 moles of 4-butoxybenzoyl chloride in 50 ml of dioxane is added over 15 minutes. The mixture is refluxed with stirring for 3 hours followed by stirring at room temperature for a further 18 hours. The mixture is filtered, and the solvent removed by rotary evaporation leaving a brown oil which is recrystallized from 25 ml of carbon tetrachloride to yield 0.73 moles of 4-butoxybenzoyl caprolactam which NMR shows to be 90% pure. The 4-butoxybenzoyl caprolactam has a melting point of approximately 87–92° C. $^1$H NMR reveals 0.9 ppm (t, 3H); 1.2–1.8 ppm (m, 12H); 2.7 ppm (m, 2H); 3.8 ppm (m, 2H); 4 ppm (t, 2H); 6.9 ppm (d, 2H); 7.5 ppm (d, 2H). $^{13}$C NMR provides 14 ppm (s); 20 ppm (s); 24 ppm (s); 29 ppm (d); 31 ppm (s); 39 ppm (s); 46 ppm (s); 68 ppm (s); 114 ppm (s); 128 ppm (s); 131 ppm (s); 162 ppm (s); 174 ppm (s); 178 ppm (s). IR (cm$^{-1}$) at 2933, 1677, 1604, 1254.

EXAMPLE V

A granular detergent composition is prepared comprising the following ingredients.

| Component | Weight % |
|---|---|
| C$_{12}$ linear alkyl benzene sulfonate | 22 |
| Phosphate (as sodium tripolyphosphate) | 20 |
| Sodium carbonate | 10 |
| Sodium silicate | 3 |
| Sodium percarbonate* | 20 |
| Ethylenediamine disuccinate chelant (EDDS) | 0.4 |
| Sodium sulfate | 5.5 |
| 4-ethoxybenzoyl caprolactam | 10 |
| Minors, filler** and water | Balance to 100% |

*Average particle size of 400 to 1200 microns.
**Can be selected from convenient materials such as CaCO$_3$, talc, clay, silicates, and the like.

Aqueous crutcher mixes of heat and alkali stable components of the detergent compositions are prepared and spray-dried. The other ingredients are admixed so that the detergent composition contains the ingredients tabulated at the levels shown.

The detergent granules with bleaching system are added together with a 6 lb. (2.7 kg) load of fabrics to a Sears KENMORE washing machine. Actual weights of detergent and ester compositions are taken to provide a 1000 ppm concentration of the detergent composition in the 17 gallon (65 1) water-fill machine. The water used has 7 grains/gallon hardness and a pH of 7 to 7.5 prior to (about 9 to about 10.5 after) addition of the detergent composition.

The fabrics are laundered at 35° C. (95° F.) for a full cycle (12 min.) and rinsed at 21° C. (70° F.).

At the end of the last rinse cycle, the test fabrics are dried in a dryer. Tristimulus meter readings (L,a,b) are then determined for each test fabric. Whiteness performance in terms of Hunter Whiteness Values (W) is then calculated according to the following equation:

$$W=(7L^2-40\ Lb)/700$$

The higher the value for W, the better the whiteness performance. In the above test, fabrics exposed to the bleaching system display significantly improved whiteness after laundering compared with fabrics which have not been exposed to the bleaching system of the invention.

EXAMPLE VI

A granular detergent is prepared by a procedure identical to that of Example V, with the exception that 20% ethylbenzoyl caprolactam is substituted for the 4-ethoxybenzoyl caprolactam bleach activator. The laundering method of Example V is repeated. In the test, all fabrics display significantly improved whiteness after laundering compared with fabrics which have not been exposed to the bleaching system of the invention.

EXAMPLE VII

A granular detergent is prepared by a procedure identical to that of Example V, with the exceptions that 10% propylbenzoyl caprolactam is substituted for the 4-ethoxybenzoyl caprolactam bleach activator. The laundering method of Example V is repeated. In the test, all fabrics display significantly improved whiteness after laundering compared with fabrics which have not been exposed to the bleaching system of the invention.

EXAMPLE VIII

A granular detergent is prepared by a procedure identical to that of Example V, with the exceptions that 5% propoxybenzoyl caprolactam is substituted for the 4-ethoxybenzoyl caprolactam bleach activator and the amount of sodium percarbonate is 10%. The laundering method of Example V is repeated. In the test, all fabrics display significantly improved whiteness after laundering compared with fabrics which have not been exposed to the bleaching system of the invention.

EXAMPLE IX

A granular detergent is prepared by a procedure identical to that of Example V, with the exceptions that 20% butoxybenzoyl caprolactam is substituted for the 4-ethoxybenzoyl caprolactam bleach activator and the amount of sodium percarbonate is 20%. The laundering method of Example V is repeated. In the test, all fabrics display significantly improved whiteness after laundering compared with fabrics which have not been exposed to the bleaching system of the invention.

EXAMPLE X

A granular detergent is prepared by a procedure identical to that of Example V, with the single exception that 15% of a 1:1 mixture of 4-butylbenzoyl caprolactam and 3-nitrobenzoyl caprolactam is substituted for the 4-ethoxybenzoyl caprolactam bleach activator. The laundering method of Example V is repeated. In the test, all fabrics display significantly improved whiteness after laundering compared with fabrics which have not been exposed to the bleaching system of the invention.

EXAMPLE XI

A granular detergent composition is prepared comprising the following ingredients.

| Component | Weight % |
|---|---|
| Anionic alkyl sulfate | 7 |
| Nonionic surfactant | 5 |
| Zeolite (0.1–10 micron) | 10 |
| Trisodium citrate | 2 |
| SKS-6 silicate builder | 10 |
| Acrylate maleate polymer | 4 |
| 2,4-dimethylbenzoyl caprolactam | 10 |
| Sodium percarbonate | 25 |
| Sodium carbonate | 5 |
| Ethylenediamine disuccinate chelant (EDDS) | 0.4 |
| Suds suppressor | 2 |
| Enzymes* | 1.5 |
| Soil release agent | 0.2 |
| Minors, filler** and water | Balance to 100% |

*1:1:1 mixture of protease, lipase, and cellulase.
**Can be selected from convenient materials such as CaCO$_3$, talc, clay, silicates, and the like.

Aqueous crutcher mixes of heat and alkali stable components of the detergent compositions are prepared and spray-dried and the other ingredients are admixed so that they contain the ingredients tabulated at the levels shown.

The detergent granules with bleaching system are added together with a 2.7 kg load of fabrics to an automatic washing machine. Actual weights of detergent and ester compositions are taken to provide a 5000 ppm concentration of the detergent composition in the 17 liter (4.5 gallon) water-fill machine. The water used has 10 grains/gallon hardness and a pH of 7 to 7.5 prior to (about 9 to about 10.5 after) addition of the detergent composition.

The fabrics are laundered at 40° C. (104° F.) for a full cycle (40 min.) and rinsed at 21° C. (70° F.).

At the end of the last rinse cycle, the test fabrics are dried in a dryer. Tristimulus meter readings (L,a,b) are then determined for each test fabric. Whiteness performance in terms of Hunter Whiteness Values (W) is then calculated according to the following equation:

$$W = (7L^2 - 40 Lb) 700$$

The higher the value for W, the better the whiteness performance. In the above test, fabrics exposed to the bleaching system display significantly improved whiteness after laundering compared with fabrics which have not been exposed to the bleaching system of the invention.

EXAMPLE XII

A granular detergent is prepared by a procedure identical to that of Example XI, with the exception that 10% ethylbenzoyl caprolactam is substituted for the 2,4-dimethylbenzoyl caprolactam bleach activator. The laundering method of Example XI is repeated. In the test, all fabrics display significantly improved whiteness after laundering compared with fabrics which have not been exposed to the bleaching system of the invention.

EXAMPLE XIII

A granular detergent is prepared by a procedure identical to that of Example XI, with the exceptions that 10% propylbenzoyl caprolactam is substituted for the 2,4dimethylbenzoyl caprolactam bleach activator. The laundering method of Example XI is repeated. In the test, all fabrics display significantly improved whiteness after laundering compared with fabrics which have not been exposed to the bleaching system of the invention.

EXAMPLE XIV

A granular detergent is prepared by a procedure identical to that of Example XI, with the exceptions that 15% propoxybenzoyl caprolactam is substituted for the 2,4-dimethylbenzoyl caprolactam bleach activator and the amount of sodium percarbonate is 30%. The laundering method of Example XI is repeated. In the test, all fabrics display significantly improved whiteness after laundering compared with fabrics which have not been exposed to the bleaching system of the invention.

EXAMPLE XV

A granular detergent is prepared by a procedure identical to that of Example XI, with the exceptions that 20% butoxybenzoyl caprolactam is substituted for the 2,4-dimethylbenzoyl caprolactam bleach activator and the amount of sodium percarbonate is 20%. The laundering method of Example XI is repeated. In the test, all fabrics display significantly improved whiteness after laundering compared with fabrics which have not been exposed to the bleaching system of the invention.

EXAMPLE XVI

A granular detergent is prepared by a procedure identical to that of Example XI, with the single exception that 15% of a 1:1 mixture of nitrobenzoyl caprolactam and nonanoyloxybenzenesul- fonate is substituted for the 2,4-dimethylbenzoyl caprolactam bleach activator. The laundering method of Example XI is repeated. In the test, all fabrics display significantly improved whiteness after laundering compared with fabrics which have not been exposed to the bleaching system of the invention.

EXAMPLE XVII

A laundry bar suitable for hand-washing soiled fabrics is prepared comprising the following ingredients.

| Component | Weight % |
|---|---|
| C$_{12}$ linear alkyl benzene sulfonate | 30 |
| Phosphate (as sodium tripolyphosphate) | 7 |
| Sodium carbonate | 15 |
| Sodium pyrophosphate | 7 |
| Coconut monoethanolamide | 2 |
| Zeolite A (0.1–10 microns) | 5 |
| Carboxymethylcellulose | 0.2 |
| Polyacrylate (m.w. 1400) | 0.2 |
| 3-chlorobenzoyl caprolactam | 6.5 |
| Sodium percarbonate | 15 |
| Brightener, perfume | 0.2 |
| Protease | 0.3 |
| CaSO$_4$ | 1 |
| MgSO$_4$ | 1 |
| Water and Filler* | Balance to 100% |

*Can be selected from convenient materials such as CaCO$_3$, talc, clay, silicates, and the like.

The detergent laundry bars are processed in conventional soap or detergent bar making equipment as commonly used in the art. Testing is conducted following the methods used in Example VI. In the test, fabrics exposed to the bleaching system display significantly improved whiteness after laundering compared with fabrics which have not been exposed to the bleaching system of the invention.

EXAMPLE XVIII

A laundry bar is prepared by a procedure identical to that of Example XVII, with the two exceptions that 15% of a 1:1:1 mixture of nitrobenzoyl caprolactam, 3-chlorobenzoyl caprolactam, and nonanoyloxybenzenesulfonate is substituted for the 3-chlorobenzoyl caprolactam bleach activator, and the level of sodium percarbonate is increated to 20%. The laundering method of Example XVII is repeated. In the test, all fabrics display significantly improved whiteness after laundering compared with fabrics which have not been exposed to the bleaching system of the invention.

EXAMPLE XIX

A laundry bar is prepared by a procedure identical to that of Example XVII, with the single exception that 15% of a 1:1 mixture of 3-methoxybenzoyl caprolactam and tetraacetyl ethylene diamine is substituted for the 3-chlorobenzoyl caprolactam bleach activator. The laundering method of Example XVII is repeated. In the test, all fabrics display significantly improved whiteness after laundering compared with fabrics which have not been exposed to the bleaching system of the invention.

EXAMPLE XX

A laundry bar is prepared by a procedure identical to that of Example XVII, with the single exception that 10% of a 1:1 mixture of 3,5,5-trimethylhexanoyloxybenzenesulfonate and 3-propoxybenzoyl caprolactam is substituted for the 3-chlorobenzoyl caprolactam bleach activator. The laundering method of Example XVII is repeated. In the test, all fabrics display significantly improved whiteness after laundering compared with fabrics which have not been exposed to the bleaching system of the invention.

EXAMPLE XXI

A laundry bar is prepared by a procedure identical to that of Example XVII, with the single exception that 10% of a 1:1 mixture of 4-butoxybenzoyl caprolactam and a benzoxazin-type bleach activator, as disclosed in U.S. Pat. No. 4,966,723, is substituted for the 3-chlorobenzoyl caprolactam bleach activator. The laundering method of Example XVII is repeated. In the test, all fabrics display significantly improved whiteness after laundering compared with fabrics which have not been exposed to the bleaching system of the invention.

EXAMPLE XXII

A bleaching system is prepared comprising the following ingredients.

| Component | Weight % |
| --- | --- |
| 4-butylbenzoyl caprolactam | 15 |
| Tetraacetyl ethylene diamine | 15 |
| Sodium percarbonate | 45 |
| Chelant (ethylenediamine disuccinate, EDDS) | 10 |
| Filler* and water | Balance to 100% |

*Can be selected from convenient materials such as $CaCO_3$, talc, clay, silicates, and the like.

Testing is conducted following the methods used in Example VI with the single exception that the an equivalent amount of the above bleaching system is substituted for the detergent composition used in Example VI. In the test, fabrics exposed to the bleaching system display significantly improved whiteness after laundering compared with fabrics which have not been exposed to the bleaching system of the invention.

While the compositions and processes of the present invention are useful in conventional laundering operations, it is to be understood that they are also useful in any cleaning system which involves low water:fabric ratios. One such system is disclosed in U.S. Pat. No. 4,489,455, Spendel, issued Dec. 25, 1984, which involves a washing machine apparatus which contacts fabrics with wash water containing detergent ingredients using a low water: fabric ratio rather than the conventional method of immersing fabrics in an aqueous bath. The compositions herein provide excellent bleaching performance in such mechanical systems. Typically, the ratio of water:fabric ranges from about 0.5:1 to about 6:1 (liters of water:kg of fabric).

EXAMPLE XXIII

Using the machine and operating conditions disclosed in U.S. Pat. No. 4,489,455, cited above, 25 grams of a composition according to Example VI herein are used to launder fabrics with concurrent bleaching. If desired, sudsing of the composition can be minimized by incorporating therein from 0.2% to 2% by weight of a fatty acid, secondary alcohol, or silicone suds controlling ingredient. In the test, all fabrics display significantly improved whiteness after laundering compared with fabrics which have not been exposed to the bleaching system of the invention.

Contrary to the teachings of U.S. Pat. No. 4,545,784, cited above, caprolactam bleach activators are preferably not absorbed onto the peroxygen bleaching compound. To do so in the presence of other organic detergent ingredients could cause safety problems. It has now been discovered that the substituted benzoyl caprolactam bleach activators of this invention can be dry-mixed with peroxygen bleaching compounds, especially perborate, and thereby avoid potential safety problems.

EXAMPLE XXIV

A laundry bar suitable for hand-washing soiled fabrics is prepared comprising the following ingredients.

| Component | Weight % |
| --- | --- |
| Linear alkyl benzene sulfonate | 30 |
| Phosphate (as sodium tripolyphosphate) | 7 |
| Sodium carbonate | 20 |
| Sodium pyrophosphate | 7 |
| Coconut monoethanolamide | 2 |
| Zeolite A (0.1–10 microns) | 5 |
| Carboxymethylcellulose | 0.2 |
| Polyacrylate (m.w. 1400) | 0.2 |
| 2-methoxybenzoyl caprolactam | 5 |
| Sodium perborate tetrahydrate | 10 |
| Brightener, perfume | 0.2 |
| Protease | 0.3 |
| $CaSO_4$ | 1 |
| $MgSO_4$ | 1 |
| Water | 4 |
| Filler* | Balance to 100% |

*Can be selected from convenient materials such as $CaCO_3$, talc, clay, silicates, and the like.

The detergent laundry bars are processed in conventional soap or detergent bar making equipment as commonly used in the art with the bleaching activator dry-mixed with the perborate bleaching compound and not affixed to the surface of the perborate. Testing is conducted following the methods used in Example VI. In the test, fabrics exposed to the bleaching system display significantly improved whiteness after laundering compared with fabrics which have not been exposed to the bleaching system of the invention.

EXAMPLE XXV

A laundry bar is prepared by a procedure identical to that of Example XXIV, with the single exception that an equivalent amount of 4-propoxybenzoyl caprolactam is substituted for the 2-methoxybenzoyl caprolactam bleach activator. The laundering method of Example XXIV is repeated. In the test, all fabrics display significantly improved whiteness after laundering compared with fabrics which have not been exposed to the bleaching system of the invention.

EXAMPLE XXVI

A laundry bar is prepared by a procedure identical to that of Example XXIV, with the exception that 10% of a 1:1 mixture of 4-butoxybenzoyl caprolactam and a bleach activator as disclosed in U.S. Pat. No. 4,634,551 is substituted for the 2-methoxybenzoyl caprolactam bleach activator. The laundering method of Example XXIV is repeated. In the test, all fabrics display significantly improved whiteness after laundering compared with fabrics which have not been exposed to the bleaching system of the invention.

EXAMPLE XXVII

A laundry bar is prepared by a procedure identical to that of Example XXIV, with the single exception that 10% of a 1:1 mixture of 3-chlorobenzoyl caprolactam and a benzoxazin-type bleach activator, as disclosed in U.S. Pat. No. 4,966,723, is substituted for the 2-methoxybenzoyl caprolactam bleach activator. The laundering method of Example XXIV is repeated. In the test, all fabrics display significantly improved whiteness after laundering compared with fabrics which have not been exposed to the bleaching system of the invention.

EXAMPLE XXVIII

A granular detergent composition is prepared comprising the following ingredients.

| Component | Weight % |
|---|---|
| Linear alkyl benzene sulfonate | 20 |
| Phosphate (as sodium tripolyphosphate) | 20 |
| Sodium carbonate | 10 |
| Sodium silicate | 3 |
| Sodium perborate tetrahydrate | 20 |
| Ethylenediamine disuccinate chelant (EDDS) | 0.4 |
| Sodium sulfate | 5.5 |
| Propoxybenzoyl caprolactam | 5 |
| Nonanoyloxybenzenesulfonate | 5 |
| Minors, filler** and water | Balance to 100% |

**Can be selected from convenient materials such as CaCO$_3$, talc, clay, silicates, and the like.

Aqueous crutcher mixes of heat and alkali stable components of the detergent compositions are prepared and spray-dried and the other ingredients are dry-mixed so that they contain the ingredients tabulated at the levels shown.

Testing is conducted following the methods used in Example VI. In the test, fabrics exposed to the bleaching system display significantly improved whiteness after laundering compared with fabrics which have not been exposed to the bleaching system of the invention.

EXAMPLE XXIX

A granular detergent is prepared by a procedure identical to that of Example XXVIII, with the exception that an equivalent amount of 2,4,6-trichlorobenzoyl caprolactam is substituted for the propoxybenzoyl caprolactam bleach activator. The laundering method of Example XXVIII is repeated. In the test, all fabrics display significantly improved whiteness after laundering compared with fabrics which have not been exposed to the bleaching system of the invention.

EXAMPLE XXX

A granular detergent is prepared by a procedure identical to that of Example XXVIII, with the single exception that an equivalent amount of pentafluorobenzyol caprolactam is substituted for the propoxybenzoyl caprolactam bleach activator. The laundering method of Example XXVIII is repeated. In the test, all fabrics display significantly improved whiteness after laundering compared with fabrics which have not been exposed to the bleaching system of the invention.

What is claimed is:

1. A method for cleaning fabrics, said method comprising contacting said fabrics in an aqueous liquor comprising a bleaching system which comprises:
   a) at least about 0.1% by weight of a peroxygen bleaching compound capable of yielding hydrogen peroxide in an aqueous solution; and
   b) at least about 0.1% by weight of one or more substituted benzoyl caprolactam bleach activators having the formula:

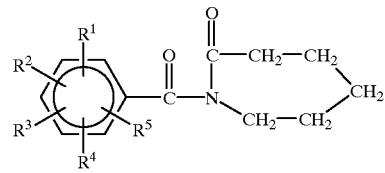

where $R^1$, $R^2$, $R^3$, $R^4$, and $R^5$ are members selected from the group consisting of H, halogen, alkyl, alkoxy, alkoxyaryl, alkaryl, alkaryloxy, and members having the structure:

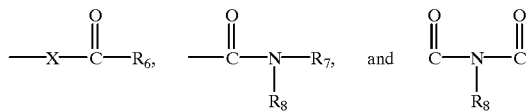

where $R_6$ is selected from the group consisting of H, alkyl, alkaryl, alkoxy, alkoxyaryl, alkaryloxy, and aminoalkyl; X is O, NH, or $NR_7$, wherein $R_7$ is H or a $C_1$–$C_4$ alkyl group; and $R_8$ is an alkyl, cycloalkyl, or aryl group containing from 3 to 11 carbon atoms; provided that at least one R substituent is not H.

2. A method according to claim 1 wherein the peroxygen bleaching compound is selected from the group consisting of sodium perborate monohydrate, sodium perborate tetrahydrate, sodium pyrophosphate peroxyhydrate, urea peroxyhydrate, sodium percarbonate, sodium peroxide and mixtures thereof.

3. A method according to claim 1 wherein said bleaching system further comprises a second bleach activator.

4. A method according to claim 3 wherein the second bleach activator is selected from the group consisting of alkanoyloxybenzenesulfonate, tetraacetyl ethylene diamine, benzoyl caprolactam, benzoxazin-type activators, peroxyacid activators having an amide moiety, and mixtures thereof.

5. A method according to claim 1 wherein the aqueous liquor has a pH of about 7.0 to about 10.5.

6. A method according to claim 1 wherein the aqueous liquor further comprises conventional detergent ingredients.

7. A method according to claim 6 wherein the conventional detergent ingredients comprise from about 5% to about 80% by weight of a detersive surfactant.

8. A method according to claim 7 wherein the conventional detergent ingredients further comprise from about 5% to about 80% by weight of a detergent builder and from 0% to about 20% by weight of conventional detersive adjunct materials.

9. A method for cleaning fabrics in washing machines having parts made of natural rubber which is susceptible to oxidative degradation, said method comprising agitating said fabrics in an aqueous liquor comprising a bleaching system which comprises:

a) at least about 0.1% by weight of a peroxygen bleaching compound capable of yielding hydrogen peroxide in an aqueous solution; and b) at least about 0.1% by weight of one or more substituted benzoyl caprolactam bleach activators having the formula:

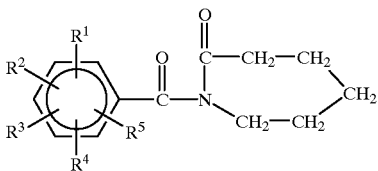

wherein $R^1$, $R^2$, $R^3$, $R^4$, and $R^5$ are members selected from the group consisting of H, halogen, alkyl alkoxy, alkoxyaryl, alkaryl, alkaryloxy, and members having the structure:

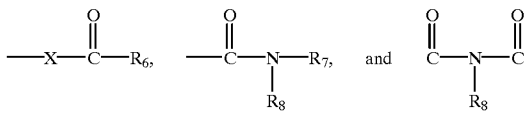

wherein $R_6$ is selected from the group consisting of H, alkyl, alkaryl, alkoxy, alkoxyaryl, alkaryloxy, and aminoalkyl; X is O, NH, or $NR_7$, wherein $R_7$ is H or a $C_1$–$C_4$ alkyl group; and $R_8$ is an alkyl, cycloalkyl, or aryl group containing from 3 to 11 carbon atoms; provided that at least one R substituent is not H; such that said natural rubber parts of said machine are substantially undamaged by the bleaching system.

* * * * *